US00PP20890P2

(12) United States Plant Patent
Saul

(10) Patent No.: US PP20,890 P2
(45) Date of Patent: Mar. 30, 2010

(54) ***AJUGA* PLANT NAMED 'DIXIE CHIP'**

(50) Latin Name: *Ajuga×tenorii*
Varietal Denomination: Dixie Chip

(75) Inventor: Richard G. Saul, Cleveland, GA (US)

(73) Assignee: Itsaul Plants, LLC, Alpharetta, GA (US)

( * ) Notice: Subject to any disclaimer, the term of this patent is extended or adjusted under 35 U.S.C. 154(b) by 6 days.

(21) Appl. No.: 12/288,774

(22) Filed: Oct. 23, 2008

(51) Int. Cl.
*A01H 5/00* (2006.01)

(52) U.S. Cl. ..... Plt./401
(58) Field of Classification Search ..... Plt./401
See application file for complete search history.

*Primary Examiner*—June Hwu
(74) *Attorney, Agent, or Firm*—Penny J. Aguirre

(57) ABSTRACT

A new cultivar of *Ajuga* plant, 'Dixie Chip', characterized by its variegated foliage that is tri-colored with mottling and blending of white, pink, and green with green veins and maturing to white with green veins with new growth that is heavily flushed with pink, its light blue flowers with non-variegated green floral leaves on racemes that are present for 4 to 6 weeks in spring, and its tight plant habit that slowly spreads by stolons with suitability as a groundcover.

2 Drawing Sheets

Botanical classification: *Ajuga×tenorii.*
Variety denomination: 'Dixie Chip'.

BACKGROUND OF THE INVENTION

The present invention relates to a new and distinct cultivar of *Ajuga* plant, botanically known as *Ajuga×tenorii* 'Dixie Chip' and will be referred to hereinafter by its cultivar name, 'Dixie Chip'. The new cultivar of *Ajuga* is a hardy herbaceous perennial grown for landscape use.

'Dixie Chip' was discovered in March of 2005 as a naturally occurring meristematic mutation of *Ajuga×tenori* 'Chocolate Chip' (not patented) in a container in his nursery in Dahlonega, Ga.

Asexual reproduction of the new cultivar was first accomplished by basal stem cuttings in June of 2005 in Alpharetta, Ga. Propagation by cuttings and division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Dixie Chip' as a unique cultivar of *Ajuga*.

1. 'Dixie Chip' exhibits variegated foliage that is tri-colored with mottling and blending of white, pink, and green with green veins and maturing to white with green veins.
2. The new growth tips on the foliage of 'Dixie Chip' are heavily flushed with pink.
3. 'Dixie Chip' exhibits blue flowers with non-variegated green floral leaves on racemes that are present for 4 to 6 weeks in spring.
4. 'Dixie Chip' exhibits a tight plant habit and slowly spreads by stolons with suitability as a groundcover.

The parent plant, 'Chocolate Chip', differs from 'Dixie Chip' in having mature foliage that is dark green to brown with new foliage that emerges deep green with a burgundy flush thus having foliage that has a darker overall appearance, in having darker blue flowers, and in having a slightly more vigorous growth habit. 'Dixie Chip' can also be compared to the cultivar 'Toffee Chip' (U.S. Plant Pat. No. 18,805) for its similarity in leaf size, plant size and foliage that is variegated with green and white. 'Toffee Chip' differs from 'Dixie Chip' in having foliage that is variegated with green centers and white margins, in having emerging foliage that lacks any pink coloration and in having variegated floral leaves.

BRIEF DESCRIPTION OF THE DRAWINGS

The accompanying colored photographs illustrate the overall appearance and distinct characteristics of the new *Ajuga*.

The photograph in FIG. 1 illustrate the foliage of 'Dixie Chip' and was taken of a two year-old plant as grown outdoors in a one gallon container in Alpharetta, Ga.

Figure 1:
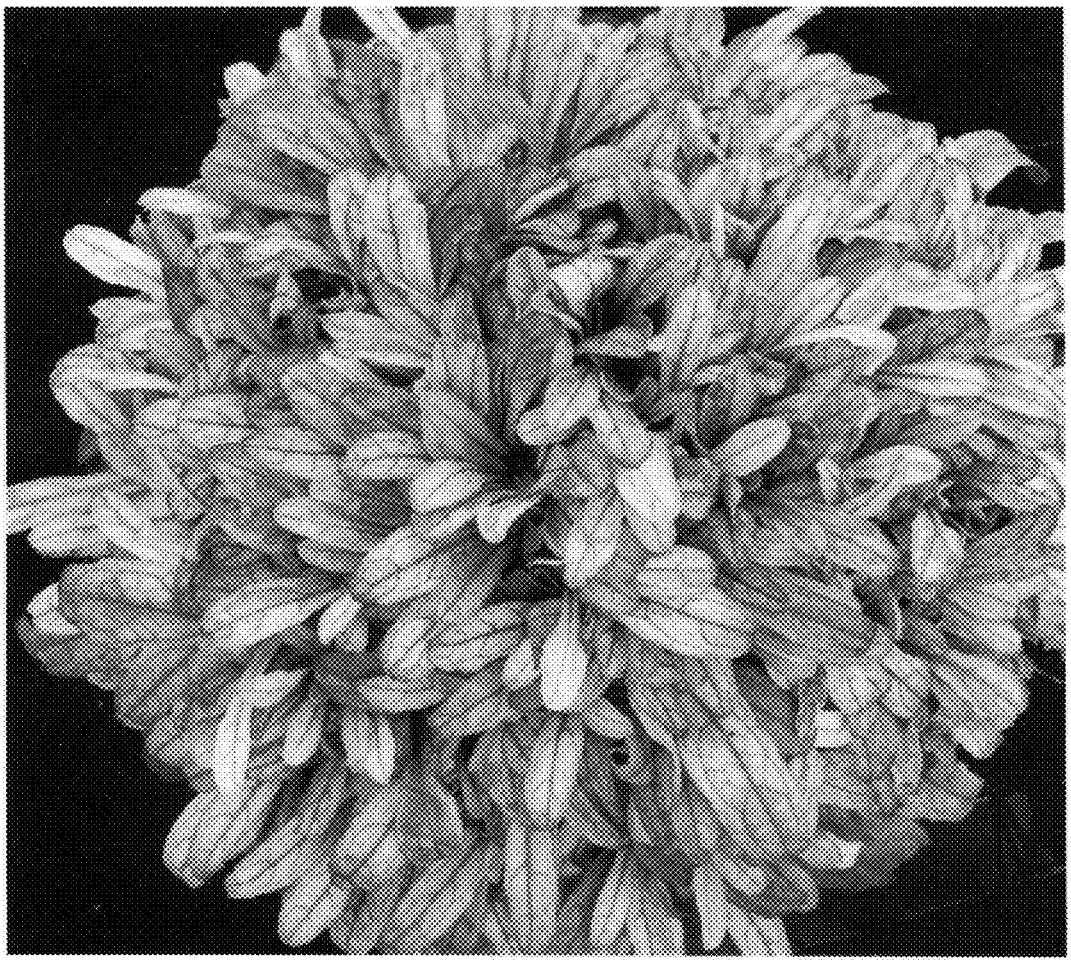
Figure 2:
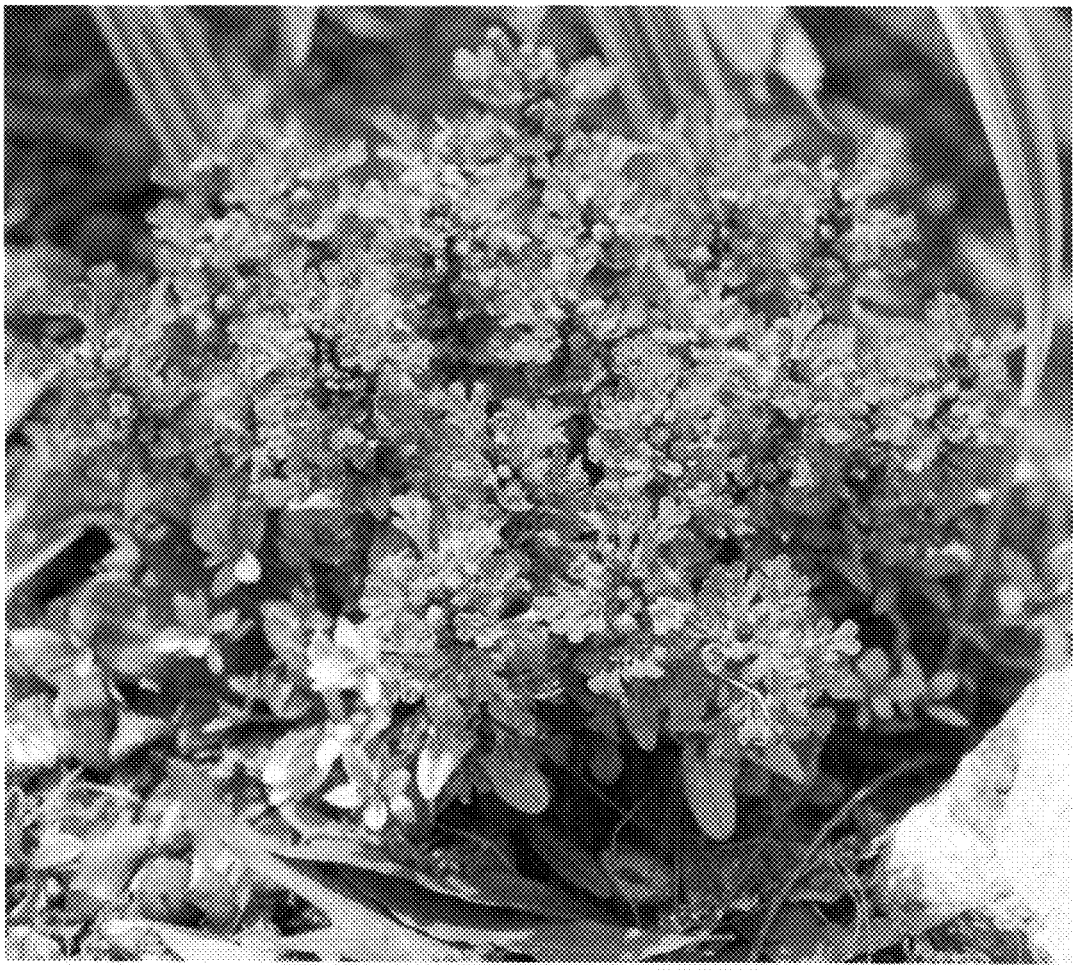

The photograph in FIG. 2 provides a view of a two year-old plant of 'Dixie Chip' as grown outdoors in a garden in Alpharetta, Ga. The colors in the photograph may differ slightly from the color values cited in the detailed botanical description, which accurately describe the colors of the new *Ajuga.*

DETAILED BOTANICAL DESCRIPTION

The following is a detailed description of the new cultivar as observed for two years in the garden in Alpharetta, Ga. with the detailed botanical data collected from one year-old plants as grown outdoors in 2-quart containers in Alpharetta, Ga. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—4 to 6 weeks in April and May in Georgia.

*Plant habit.*—Herbaceous perennial, tightly compact and slowly spreading by stolons.

*Height and spread.*—Reaches about 5 cm in height (foliage) and about 15 cm in width.

*Hardiness.*—U.S.D.A. Zones 5 to 9.

*Diseases pest.*—Highly Disease and pest free under the conditions tested.

*Root description.*—Fibrous roots on short rhizomes, roots 158D in color, rhizomes about 15 cm in length and 35 mm in width.

*Stolons.*—145B and 147B in color and an average of 25 cm in length and 1.5 mm in width.

*Branching habit.*—Basal rosettes of leaves from rhizomes.

*Propagation.*—Basal stem cuttings and division.

*Root initiation.*—Roots initiate on cuttings in 7 to 9 days at 75° F. in a greenhouse under mist.

*Root development.*—Rooted cuttings fully develop at least a 72-cell plug in 4 to 5 weeks under greenhouse conditions without supplemental lighting in all seasons.

*Growth rate.*—Moderate.

Foliage description:

*Leaf shape.*—Spatulate.

*Leaf division.*—Simple.

*Leaf base.*—Truncate to base of rhizome.

*Leaf apex.*—Broadly acute to rounded.

*Leaf venation.*—Pinnate, 138A in color on upper surface and 138B in color on lower surface, conspicuous (particularly on mature leaves).

*Leaf margins.*—Entire.

*Leaf attachment and arrangement.*—2-ranked from rhizome.

*Leaf orientation.*—Emerge upright and then slightly recurve.

*Leaf surface.*—Finely puberulent on upper and lower surface.

*Leaf color.*—Upper surface, newly emerged foliage; mottled variegation pattern of 59B to 59D to 63C with 147A, lower surface, newly emerged foliage; 147B with some mottling of 159D to 75D, mature foliage upper and lower surface; mottling of 155A to ID with N138B and 144C.

*Leaf size.*—Mature to about 6 cm in length and 1.5 cm in width.

*Leaf quantity.*—Average of 16 per rhizome, about 300 in a clump 15 cm in diameter.

*Leaf attachment.*—Sessile.

Flower description:

*Inflorescence type.*—Raceme of dense whorls of bilabiate flowers.

*Inflorescence size.*—About 14 cm in height and 2 cm in width.

*Inflorescence number.*—An average of 50 as grown in a one-gallon container.

*Lastingness of inflorescence.*—Individual flowers last 2 to 3 days.

*Flower type.*—Bilabiate.

*Flower number.*—About 2 to 5 flowers per whorl, about 35 per raceme.

*Flower fragrance.*—None.

*Flower buds.*—Oblong in shape, about 9 mm in length and 3 mm in diameter, villose surface, color of apex is a blend of 97A and 97C, color of calyx portion 138B.

*Flower size.*—About 1.1 cm in length and about 6 mm in diameter.

*Peduncles.*—An average of 14 cm in length and 3 mm in width, villose surface and 147A in color.

*Pedicels.*—None, sessile.

*Calyx.*—5-pointed, star-shaped, about 3 mm in height and 3 mm in width, persistent.

*Sepals.*—5, elliptic in shape, about 1.5 mm in width and 3 mm in length, 138A to 138B in color on both surfaces, pubescent on both surfaces, margin is entire and villose.

*Petals.*—2 segments with shorter upper lip and a spreading lower lip with both segment fused into tube that is about 6 mm in length and 1 to 2 mm in width, upper lip has 2 oblong-shaped lobes fused together with apex free and acute with free portion about 1 mm in length and 2 mm in width, lower lip has 4 lobes; 2 oblong side lobes that spread sideways and are slightly reflexed with a broadly acute apex with free portion about 4 mm in length and 1.5 mm in width and 2 center lobes that are oblanceote in shape and slightly reflexed with a rounded apex with a broadly acute to rounded apex with free portion about 4 mm in length and 1.5 mm in width and 2 center lobes that are oblanceote in shape and slightly reflexed with a rounded apex and with free portion about 4 mm in length and 1.5 mm in width, all segments have entire margins, are pubescent on the outer surfaces and glabrous on the inner surfaces, color of inner surfaces is 96B to 96C with stripes of 97C to 97D, color of tube and outer surfaces is a blend of 91A, 91B, 97A and 97B.

*Bracts.*—2 per floral whorl, average of 1.2 cm in length and 1 cm in width, elliptic in shape, sessile, acute apex, truncate base, surface is puberulent on upper and lower surface, color a blend of 147A and 138A on upper surface and 138B on lower surface.

Reproductive organs:

*Pistils.*—1, style with stigma is about 9 mm in length, 0.5 mm in width and 91D in color and translucent.

*Stamens.*—4, filament is about 7 mm in length, 0.3 mm in width and 91B in color, anthers are oblong in shape and 203B in color, pollen is abundant in quantity and 15B in color.

*Fruit.*—Fruit and seed production was not observed under the conditions tested.

It is claimed:

1. A new and distinct variety of *Ajuga* plant named 'Dixie Chip' as described and illustrated herein.

* * * * *